United States Patent
Burke et al.

(10) Patent No.: US 10,173,004 B2
(45) Date of Patent: Jan. 8, 2019

(54) FLOW ACTUATED VALVE FOR IMPLANTABLE DRUG DELIVERY DEVICE

(71) Applicant: Flowonix Medical Incorporated, Mt. Olive, NJ (US)

(72) Inventors: Paul Burke, Bellingham, MA (US); Steve Adler, Randolph, NJ (US); Benjamin Piecuch, Providence, RI (US); Steve Hantman, Franklin, MA (US)

(73) Assignee: Flowonix Medical Incorporated, Mt. Olive, NJ (US)

( * ) Notice: Subject to any disclaimer, the term of this patent is extended or adjusted under 35 U.S.C. 154(b) by 999 days.

(21) Appl. No.: 14/136,948

(22) Filed: Dec. 20, 2013

(65) Prior Publication Data

US 2014/0194851 A1 Jul. 10, 2014

Related U.S. Application Data

(60) Provisional application No. 61/750,111, filed on Jan. 8, 2013.

(51) Int. Cl.
*A61M 5/168* (2006.01)
*A61M 5/142* (2006.01)
*A61M 39/24* (2006.01)

(52) U.S. Cl.
CPC .... *A61M 5/16881* (2013.01); *A61M 5/14276* (2013.01); *A61M 2039/242* (2013.01); *A61M 2039/2413* (2013.01); *A61M 2039/2433* (2013.01); *A61M 2039/2466* (2013.01); *A61M 2039/2473* (2013.01)

(58) Field of Classification Search
CPC .......... A61M 5/14276; A61M 5/16881; A61M 2039/2413; A61M 2039/2433; A61M 2039/2473; A61M 2039/2486
See application file for complete search history.

(56) References Cited

U.S. PATENT DOCUMENTS

| | | | |
|---|---|---|---|
| 4,838,887 A * | 6/1989 | Idriss | A61M 5/14276 128/DIG. 12 |
| 5,049,141 A | 9/1991 | Olive | |
| 5,069,663 A | 12/1991 | Sussman | |

(Continued)

FOREIGN PATENT DOCUMENTS

WO   WO 2010086476 A1 *  8/2010  ............ A61M 39/24

OTHER PUBLICATIONS

Notification Concerning Transmittal of International Preliminary Report on Patentability issued in International Application No. PCT/US2014/010465 dated Jul. 14, 2015.

(Continued)

*Primary Examiner* — Shefali D Patel
(74) *Attorney, Agent, or Firm* — The Marbury Law Group, PLLC

(57) ABSTRACT

An "MRI-safe" implantable infusion apparatus and a method that include a flow actuated valve (FAV) that closes to prevent a free flow of an infusate to a patient during an MRI procedure, and a release mechanism that opens the valve so that the apparatus may return to normal operation following the MRI procedure. In this manner, patient safety is improved and an inconvenience of having to empty a pump reservoir before undergoing the MRI procedure may be avoided.

26 Claims, 12 Drawing Sheets

(56) References Cited

U.S. PATENT DOCUMENTS

| | | | |
|---|---|---|---|
| 7,510,552 B2 * | 3/2009 | Lebel | A61K 9/0024 604/891.1 |
| 8,273,058 B2 | 9/2012 | Burke et al. | |
| 2003/0139699 A1 | 9/2003 | Rosenberg | |
| 2005/0273081 A1 | 12/2005 | Olsen | |
| 2006/0116665 A1 | 6/2006 | Gilbert | |
| 2009/0093797 A1 * | 4/2009 | Burke | A61M 5/14276 604/891.1 |
| 2012/0024987 A1 | 2/2012 | Nagele Nacken | |

OTHER PUBLICATIONS

International Search Reported and Written Opinion received for International Application No. PCT/US2014/010465, dated Jun. 3, 2014.

Extended European Search Report issued for European Patent Application No. 14737660.2-1662; Reference No. 111733P756PCEP; dated Sep. 9, 2016.

Supplemental European Search Report issued for European Patent Application No. 14737660.2-1662; Reference No. 111733P756PCEP; dated Sep. 27, 2016.

* cited by examiner

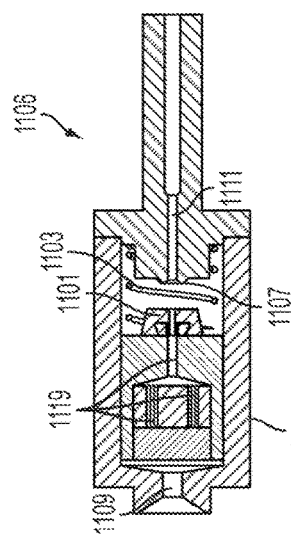
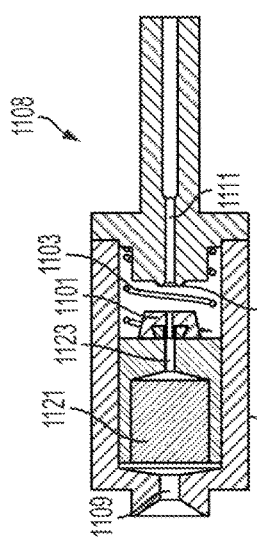
FIG. 11D
FIG. 11E
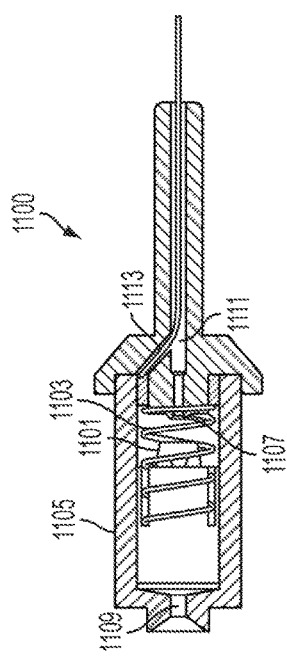
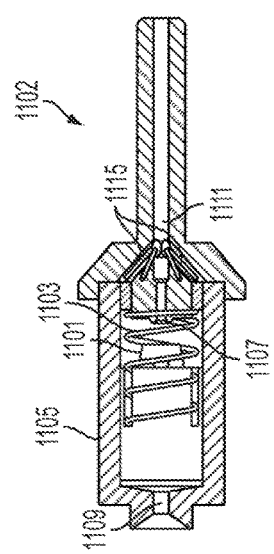
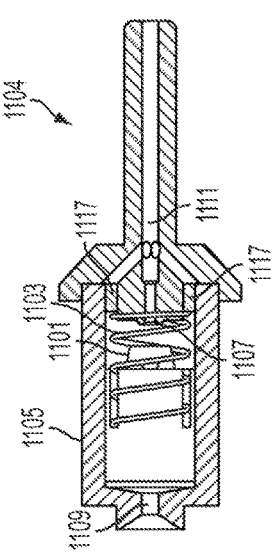
FIG. 11A
FIG. 11B
FIG. 11C

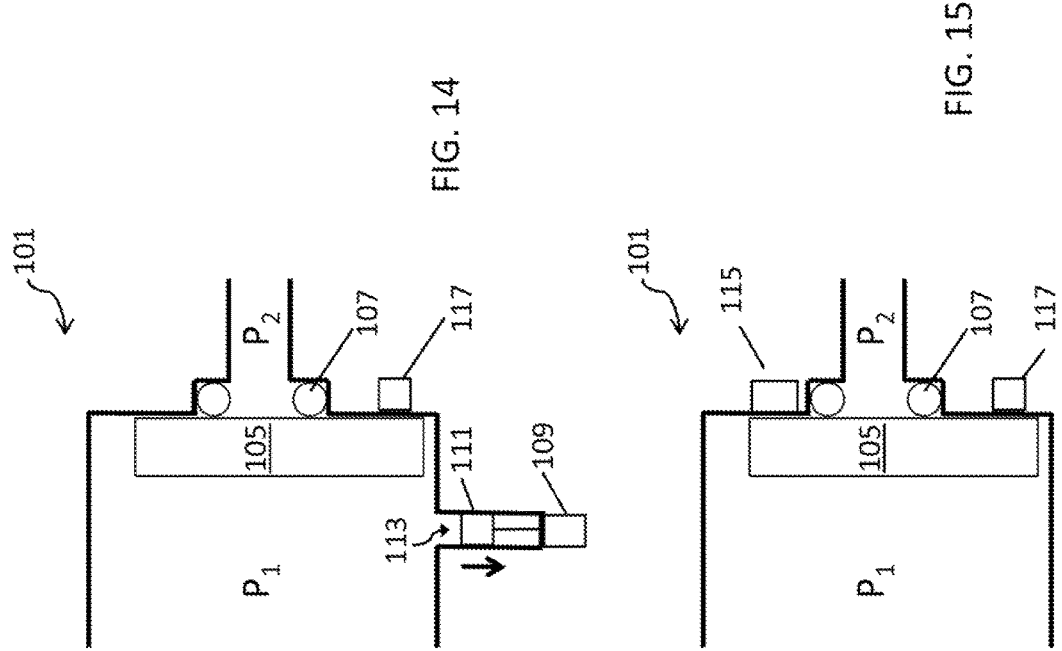

FLOW ACTUATED VALVE FOR IMPLANTABLE DRUG DELIVERY DEVICE

RELATED APPLICATION

This application claims the benefit of priority to U.S. Provisional Application No. 61/750,111, filed Jan. 8, 2013, the entire contents of which are incorporated herein by reference.

FIELD

The present invention relates generally to implantable infusion devices for the delivery of medication or other fluids to a patient.

BACKGROUND

Various implantable devices exist for delivering infusate, such as medication, to a patient. One such device is an implantable valve accumulator pump system. This system includes an electronically controlled metering assembly located between a drug reservoir and an outlet catheter. The metering assembly may include two normally closed solenoid valves that are positioned on the inlet and outlet sides of a fixed volume accumulator. The inlet valve opens to admit a fixed volume of infusate from the reservoir into the accumulator. Then, the inlet valve is closed and the outlet valve is opened to dispense the fixed volume of infusate from the accumulator to an outlet catheter through which the infusate is delivered to the patient. The valves may be controlled electronically via an electronics module, which can optionally be programmed utilizing an external programmer to provide a programmable drug delivery rate. The metering assembly is designed such that the inlet valve and the outlet valve are never simultaneously open.

This type of implantable infusion device is highly effective in most situations. However, when a patient with such a device enters an MRI (magnetic resonant imaging) machine and the machine is activated, the large magnetic fields may affect the operation of the pump's valves which could cause the metering function of the accumulator to be bypassed. In some cases, the inlet and outlet valves of the pumps may open simultaneously, creating a severe safety risk for the patient. Consequently, patients implanted with these devices must be instructed to have the pump reservoir emptied before undergoing an MRI procedure. This prohibition and warning is commonplace for patients implanted with such medical devices. Requiring implanted medical devices to be emptied before an MRI procedure adds to the cost of the procedure and may delay the procedure.

SUMMARY

Various embodiments include an "MRI-safe" implantable infusion apparatus and method that includes a flow actuated valve (FAV) that closes to prevent a free flow of infusate to a patient during an MRI procedure, and a release mechanism that opens the valve so that the device may return to normal operation following the MRI procedure. In this manner, patient safety is improved and the inconvenience of having to empty the pump reservoir before undergoing an MRI procedure may be avoided.

Embodiments include an implantable infusion apparatus that includes an infusate reservoir, a metering assembly receiving infusate from the reservoir and outputting a metered quantity of infusate at a first flow rate, an outlet delivering the metered quantity of infusate to a delivery site, and a flow activated valve in a fluid path between the reservoir and the outlet, the flow activated valve maintaining an open position allowing infusate to flow through the valve at the first flow rate and closing when the rate of flow of the infusate through the valve exceeds a threshold flow rate, greater than the first flow rate.

Various embodiments of the implantable infusion apparatus include a release mechanism that is operable to re-open the flow activated valve through a passive or active re-set mechanism.

Further embodiments include a method of delivering infusate to a delivery site within a human or animal body using an implantable infusion apparatus that may include flowing a metered quantity of infusate from an infusate reservoir through a flow activated valve to the delivery site at a first infusate flow rate, and closing the flow activated valve to restrict the flow of infusate to the delivery site when a flow rate of the infusate through the flow activated valve exceeds a threshold flow rate, greater than the first flow rate.

In various embodiments, the method may further include reopening the flow activated valve, and flowing a metered quantity of infusate through the flow activated valve to the delivery site.

Further embodiments include an implantable infusion apparatus that includes means for flowing a metered quantity of infusate from an infusate reservoir through a flow activated valve to the delivery site at a first infusate flow rate, and means for closing the flow activated valve to restrict the flow of infusate to the delivery site when a flow rate of the infusate through the flow activated valve exceeds a threshold flow rate, greater than the first flow rate. The apparatus may further include means for re-opening the flow activated valve.

BRIEF DESCRIPTION OF THE DRAWINGS

The accompanying drawings, which are incorporated herein and constitute part of this specification, illustrate example embodiments of the invention, and together with the general description given above and the detailed description given below, serve to explain the features of the invention.

FIGS. 11A-E illustrate embodiments of a FAV having a restrictive flow path passive release mechanism.

FIG. 14 schematically illustrates an active FAV release mechanism according to one embodiment.

FIG. 15 schematically illustrates an active FAV release mechanism according to another embodiment.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

Various embodiments include implantable drug delivery systems and methods for delivering metered doses of a drug or other infusate that include a flow actuated valve (FAV) that prevents a free flow of the infusate to the patient in the event of a fault condition, including bypass or failure of a metering assembly. In embodiments, the FAV is actuated (e.g., closes) to prevent unrestricted flow to the patient in the event where the implantable drug delivery system is exposed to a large magnetic field, such as during an MRI procedure, that causes electromagnetically-actuated valves (e.g., solenoid valves) of the metering assembly to open. The FAV may be a bi-stable valve that maintains an open position, allowing infusate to pass during normal operation of the device, and closes when the flow rate through the valve exceeds a threshold flow rate indicative of a fault condition. Embodiments may further include a release mechanism that causes the FAV to return to an open position, so that metered flow of the infusate to the patient may be resumed.

Various embodiments may provide an "MRI-safe" implantable drug infusion device that includes a flow actuated valve (FAV) that closes to prevent a free flow of infusate to a patient during an MRI procedure, and a release mechanism that opens the FAV so that the device may return to normal operation following the MRI procedure. In this manner, patient safety is improved and the inconvenience of having to empty the pump reservoir before undergoing an MRI procedure may be avoided.

Figure 1:
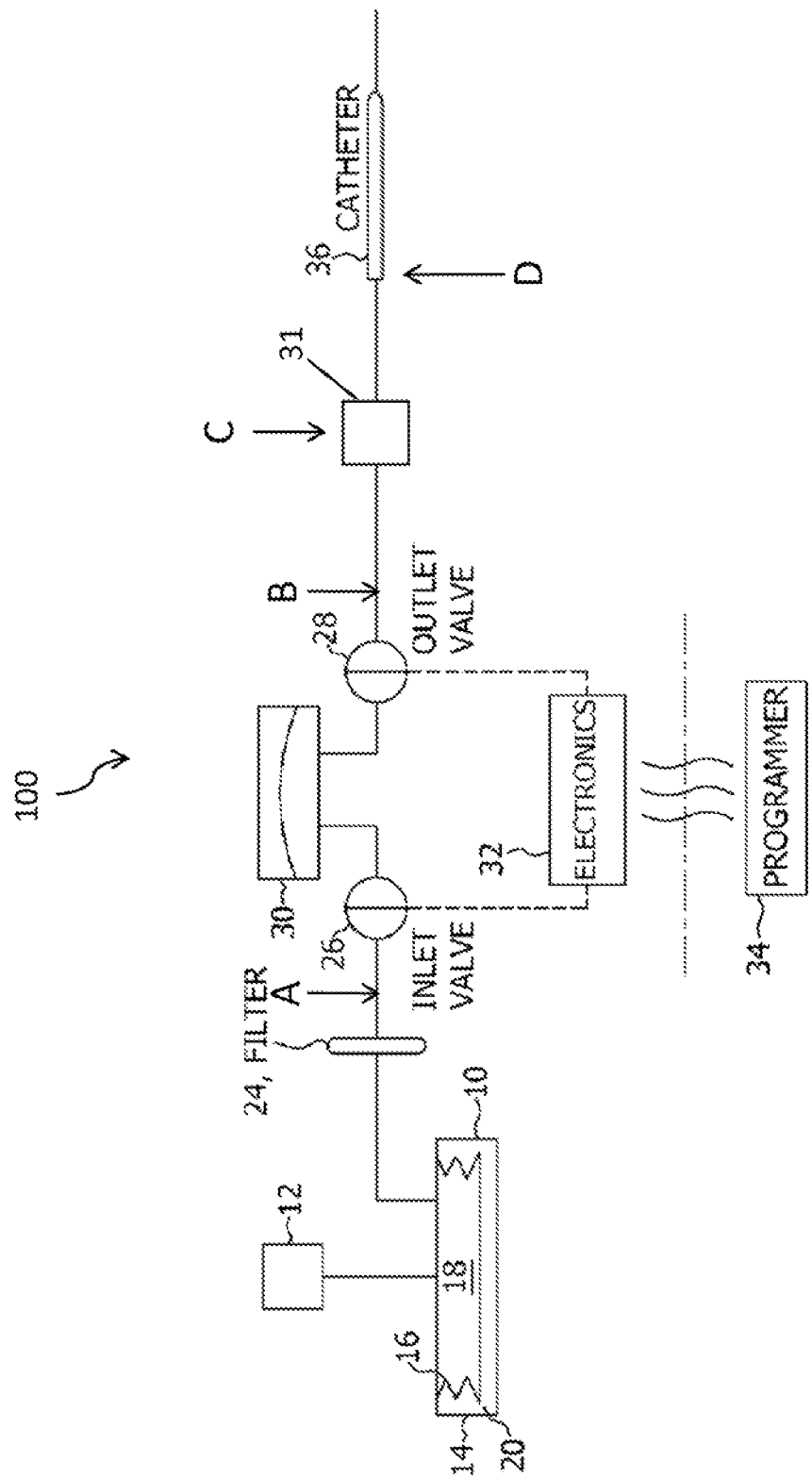
FIG. 1 is a schematic diagram of an implantable drug delivery system.
Figure 2:
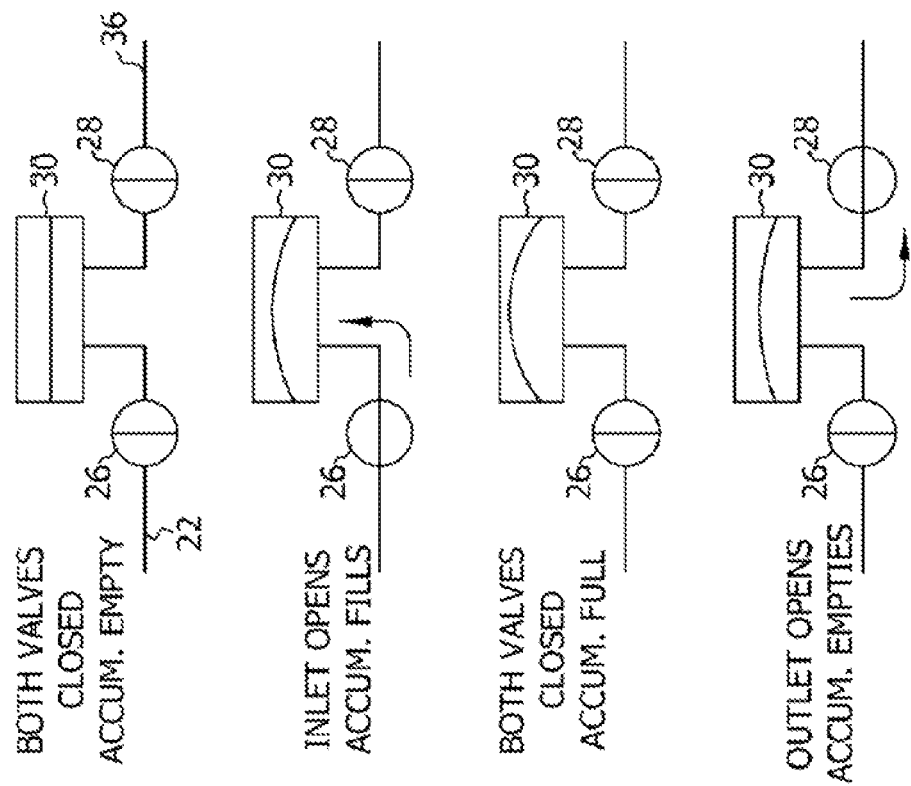
FIG. 2 schematically illustrates the sequence of steps performed by the metering assembly of the implantable drug delivery system.
Figure 3:
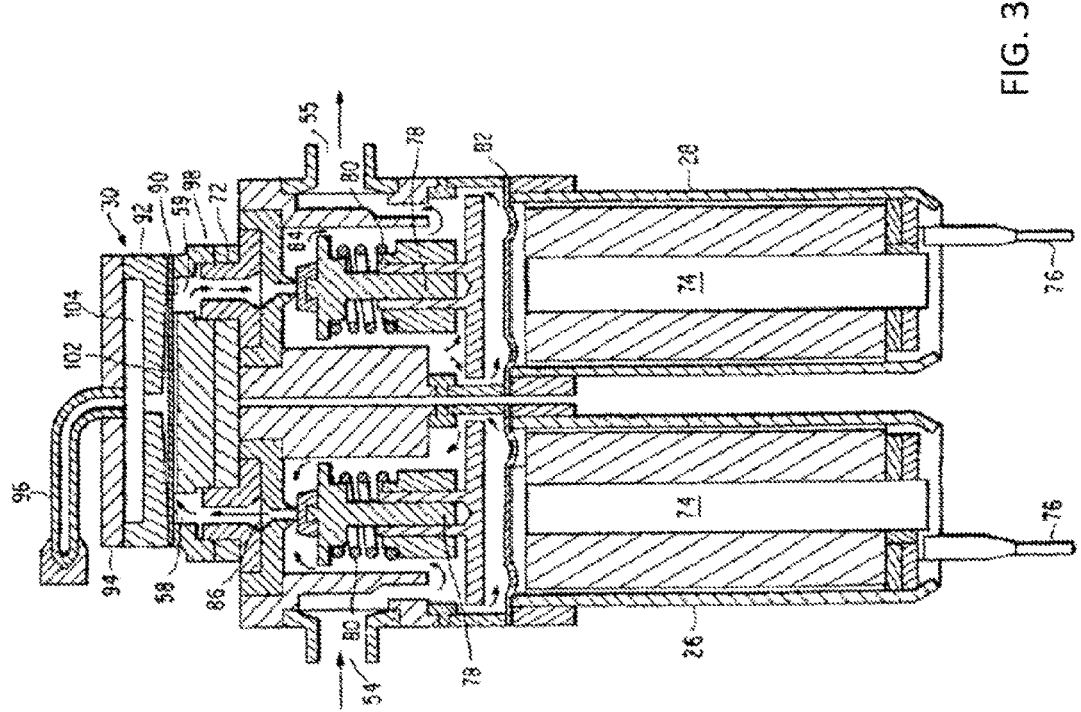
FIG. 3 is a cross-section view of the metering assembly.

FIGS. 1-3 illustrate an embodiment of an implantable valve accumulator pump system 100 for the delivery of infusate, such as medication. Various details of such a system are described, for example, in U.S. Pat. Nos. 4,838,887, 5,049,141 and 8,273,058, the entire teachings of which are incorporated herein by reference. The system 100 may generally include four assemblies, as shown in FIG. 1. The first major assembly is a rechargeable, constant pressure drug reservoir 10 in series with a bacteria/air filter 24. In one embodiment, the reservoir 10 comprises a sealed housing 14 containing a bellows 16. The bellows 16 separates the housing 14 into two parts. Chamber 18 is used to hold the drug or other medicinal fluid. Second zone 20 is normally filled with a two-phase fluid, such as Freon®, that has a significant vapor pressure at body temperature. Thus, as the fluid within the second zone 20 vaporizes, it compresses the bellows 16, thereby pressurizing the drug in the chamber 18. The drug can be refilled via septum 12.

The two-phase fluid helps maintain the chamber 18 under a constant pressure. When the chamber is refilled, the two-phase fluid is pressurized thereby condensing a portion of the vapor and converting it to liquid. As the chamber 18 is emptied, this liquid vaporizes, thus maintaining the pressure on the bellows 16.

Since the infusate in chamber 18 is under positive pressure, it is urged out of the chamber, through a bacterial filter 24 and toward the metering assembly.

The second major assembly is an electronically controlled metering assembly comprising two normally closed solenoid valves 26, 28, which are positioned on the inlet and outlet sides of a fixed volume accumulator 30. The valves are controlled electronically via an electronics module 32, which can be programmed utilizing an external programmer 34. The metering assembly is designed such that the inlet valve 26 and the outlet valve 28 are never simultaneously open.

The third major assembly is an outlet catheter 36 for medication infusion in a localized area. The delivery of fluid occurs at an infusion site that is below the accumulator pressure, thereby forcing discharge through the catheter 36.

The drug reservoir and electronically controlled metering assembly may be contained within a biocompatible housing, also containing a power source (e.g., battery), that may be implanted within the body of a human or animal patient. The outlet catheter may be integral with the housing, or may be a separate component that is attached to the housing. An access port 31, in communication with the catheter 36, may be provided downstream of the metering assembly. The access port 31 may be used, for example, to manually provide a bolus dose of medication to the patient.

The fourth assembly of the system of FIG. 1 is an external programmer 34 used to communicate and program the desired medication regimen. This programmer is preferably a handheld unit with a touch screen. It provides a (wireless) data transfer link to the implanted electronics 32 and is able to exchange information with the electronics 32, including but not limited to battery status, diagnostic information, calibration information, etc. Those skilled in the art will appreciate that an external programmer is not necessary; for example, the device could be used in a fixed rate configuration that is not programmed but is preset.

Returning to the metering assembly, FIG. 2 illustrates the normal sequence used to fill and dispense infusate. The valves in the medication metering assembly alternately open and close to admit infusate from the reservoir 18 into the accumulator 30, via conduit 22, and to dispense a precise volume spike to an outlet catheter 36. During the first step, both valves are closed and the accumulator is empty. In this step, no fluid is moved. During the second step, the inlet valve 26 opens while the outlet valve 28 remains closed. Since the incoming fluid is at a higher pressure than the accumulator 30, fluid fills the accumulator. The accumulator preferably has a fixed volume such that exact amounts of fluid can be dispensed. Once the accumulator 30 is filled, no fluid movement occurs. During the third step, the inlet valve 26 closes, thereby separating the reservoir from the accumulator. At this step, the accumulator 30 is filled. Finally, during the fourth step, the outlet valve 28 opens. Since the accumulator 30 is at a higher pressure than the outlet canella, the fluid exits the accumulator through outlet valve 28.

FIG. 3 illustrates the components used in the metering assembly. Valves 26 and 28 are implemented as miniature solenoid valves. The valves are preferably disposed in a side-by-side arrangement having two solenoid assemblies 74, each receiving power via a corresponding electrical lead 76. The valves are operably powered to drive a working plunger 78 biased by means of spring 80. The working plunger and return spring assembly are isolated from the solenoids 74 by means of an isolation diaphragm 82. As is customary, the solenoid is actuated by a magnetic field that drives the working plunger 78. Once charged, the solenoid overcomes the force of the bias spring 80, and pulls the plunger 78 off the valve seat 84, allowing fluid flow.

The flow path of the infusate or medicinal fluid is illustrated by the arrows in FIG. 3. As described above, with valve 26 in the open position, fluid communication is established between the accumulator 30 and the inlet conduit 54. The infusate is thereby delivered upward through the valve seat 84 (shown closed in FIG. 3), into the accumulator flow passage 86. The area between the valve seats comprises the accumulator storage space. When valve 26 is closed, the accumulator 30 is isolated from the reservoir 18.

When valve 28 is opened, fluid communication is established between the accumulator and the outlet conduit 55. The infusate is thereby delivered downward from the accumulator storage space, through the valve seat 84 (shown closed in FIG. 3), and into the outlet conduit 55. Furthermore, the system is preferably designed such that valves 26 and 28 cannot be opened at the same time in order to prevent the metering function of the accumulator 30 from being bypassed.

Implantable drug pumps such as described above may not be fully MRI compatible. This is because the valves in such devices are typically actuated by magnetic fields, such as solenoid valves 26 and 28, described above. Thus, a patient with an implanted drug pump may undergo an MRI procedure, and in the right configuration, the direction of the magnetic field in the MRI system could cause both valves to open simultaneously. In such a case, the drug can flow freely from the positive-pressure drug reservoir 10 to the patient, resulting in an overdose or even death of the patient. Consequently, if a patient needs to undergo an MRI procedure, the drug needs to be removed from the reservoir prior to the procedure, and replaced following the procedure. This is a significant inconvenience to both the patient and medical practitioners. Occasionally, the patient or practitioners may forget to empty the drug reservoir prior to the MRI procedure, which creates an unacceptable safety risk.

Accordingly, various embodiments include implantable drug delivery systems and methods for delivering metered doses of a drug or other infusate that include a flow actuated valve (FAV) in a fluid path between the drug reservoir 10 and the patient. The FAV is actuated (e.g., closes) to prevent unrestricted flow to the patient in the event that the valves 26, 28 are opened simultaneously, such as in the presence of a strong external magnetic field (e.g., during an MRI procedure). Thus, an implantable drug pump with a FAV may be fully compatible with MRI procedures, or "MRI safe."

The FAV may be a bi-stable valve that maintains an open position, allowing infusate to pass during normal operation of the device. The FAV closes when the flow rate through the FAV exceeds a threshold flow rate, which is greater than the maximum expected flow rate during normal (metered) operation of the drug pump. The FAV may be configured so that normal pump flow does not close the valve, but the FAV does close due to a high pressure/flow condition (i.e., the large pressure drop, such as 25 pisg, across the FAV when both valves 26, 28 are open). The FAV may be designed to close in all MRI situations while preventing false triggers, allowing for reset, aspiration, and bolus. Some leakage through or around the FAV during or following FAV closure may be acceptable, as described further below.

A FAV may be located in any position along a flow path between the drug reservoir 10 and the patient. Referring to FIG. 1, for example, the FAV may be located at position A (i.e., between the drug reservoir 10 and the valve set 26, 28 of the metering assembly), position B (i.e., between the valve set 26, 28 and an access port 31), position C (within the access port 31), or position D (at or near the catheter connection point or within the catheter 36). Other suitable locations for the FAV could also be utilized. An advantage of positions A, B and C is that the FAV may not be triggered by or interfere with the delivery of a bolus dose through access port 31. An advantage of positions B, C and D is that a closed FAV may be reset (i.e., re-opened) by venting through the access port 31. Other passive and active mechanisms for resetting (opening) the FAV may be utilized, as described in further detail below.

Figure 4A:
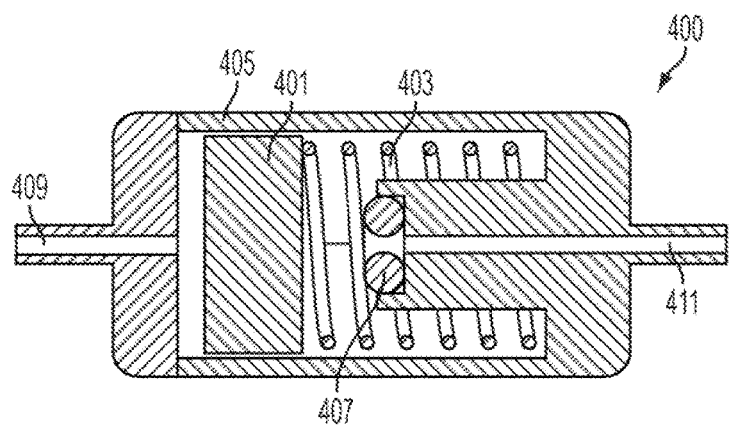
FIGS. 4A-C illustrate a flow actuated valve (FAV) including a spring and slidable piston assembly according to one embodiment.
Figure 4B:
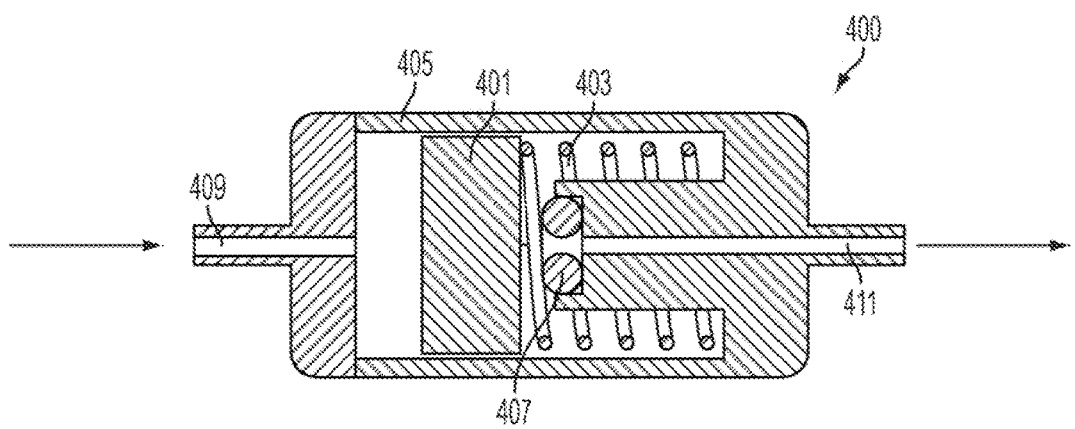
Figure 4C:
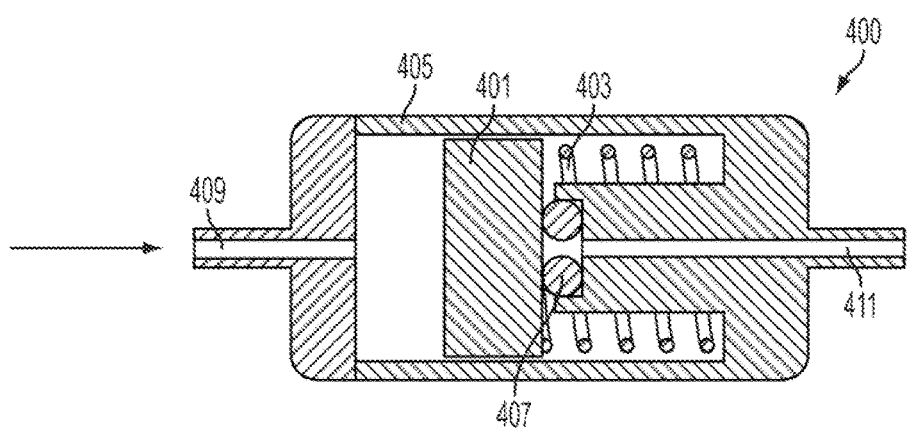

FIGS. 4A-4C illustrate a FAV 400 according to one embodiment of the invention. The FAV 400 in this embodiment includes a piston 401 and spring member 403 within a housing 405. The piston 401 may comprise any suitable material, such as titanium. In embodiments, the piston 401 and/or spring member 403 may comprise non-magnetic materials (i.e., negligibly influenced by an external magnetic field). The spring member 403 is attached at one end to the piston 401 and at the opposite end to the housing 405. The piston 401 may reciprocate within the housing 405. FIG. 4A illustrates the piston 401 in a home or rest position. In this position, the spring member 403 maintains the piston 401 a distance away from a valve seat 407, which may be an o-ring. Fluid, such as a liquid drug or other infusate, may enter the housing 405 via an inlet opening 409, as shown in FIG. 4A. The fluid may pass around and/or through openings in the piston 401 and exit the housing 405 through an outlet opening 411. Fluid pressure from the fluid causes the spring member 403 to compress and the piston 401 to displace in the direction of the valve seat. During normal (e.g., metered) operation of the drug pump, the fluid pressure is not sufficient to cause the piston 401 to contact against the valve seat 407. At or above a threshold flow rate, the fluid pressure against the piston 401 causes the spring member 403 to compress sufficiently so that the piston 401 contacts and seals against the valve seat 407. The fluid is thus blocked from exiting the housing 405 through the outlet opening 411.

Figure 5B:
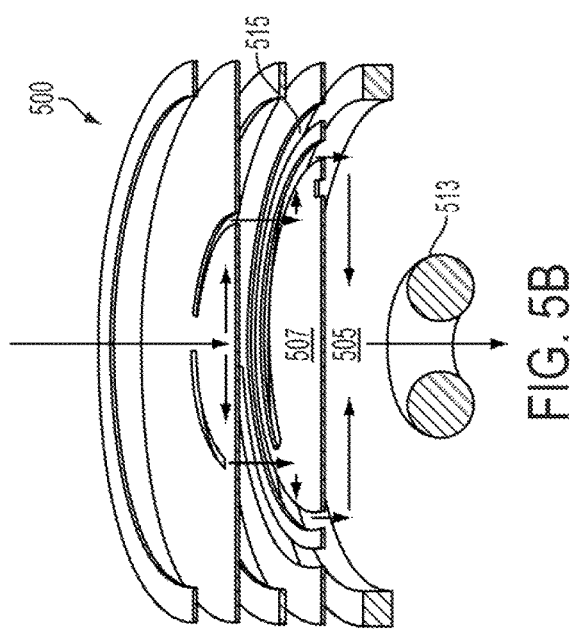
FIGS. 5A-C illustrate a flow actuated valve (FAV) including a spring diaphragm according to another embodiment.
Figure 5C:
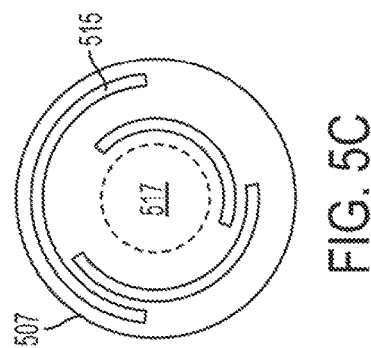
Figure 5A:
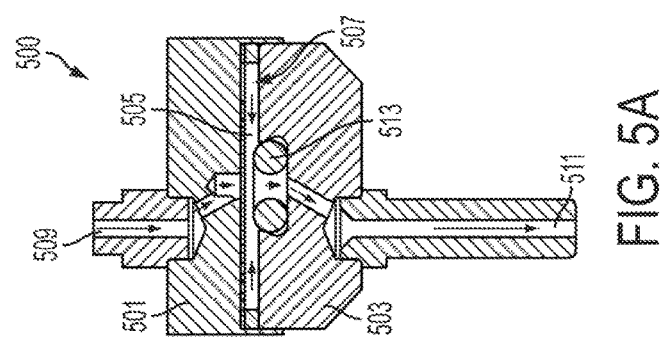

FIGS. 5A-5C illustrate an alternative embodiment of a flow activated valve (FAV) 500 which may be used in an implantable drug pump as described above. FIG. 5A is a cross-sectional side view of the FAV 500, FIG. 5B is an exploded cross-sectional view of several components of the FAV 500, and FIG. 5C is a plan view of a diaphragm 507 according to one embodiment. As shown in FIG. 5A, the FAV 500 includes a first member 501 that is engaged to a second member 503 to define a fluid chamber 505 therebetween. An inlet conduit 509 extends through the first member 501 to the fluid chamber 505, and an outlet conduit 511 extends through the second member 503 to the fluid chamber 505. A valve seat 513, which may be an o-ring, is located on one end of the fluid chamber 505 proximate the outlet conduit 511. A diaphragm 507, which may be a spring diaphragm, is secured between the first and second members 501, 503 and extends across the fluid chamber 505. The diaphragm 507 may be a circular disk of a thin metal sheet. The diaphragm 507 may be made of a suitable material, such as titanium. Preferably, the diaphragm 507 is comprised of a non-magnetic material (i.e., negligibly influenced by an external magnetic field). As shown in FIG. 5C, the diaphragm 507 may comprise a solid central region 517 and may have one or more openings 515 in a peripheral region.

In operation, fluid, such as a liquid drug or other infusate, enters the fluid chamber 505 via inlet conduit 509. The fluid contacts the diaphragm 507 flows through the one or more openings 515 in the periphery of the diaphragm 507, as shown in FIG. 5B. The fluid then exits the fluid chamber 505 via the outlet conduit 511. Fluid pressure from the fluid in the chamber 505 urges the diaphragm 507 to deflect in the direction of the valve seat 513. The diaphragm 507 may have a spring force that resists deflection against the valve seat 513 during normal (e.g., metered) operation of the drug pump. At or above a threshold flow rate, the fluid pressure against the diaphragm 507 is sufficient to case the diaphragm 507 to deflect sufficiently so that the solid central region 517 of the diaphragm 507 contacts and seals against the valve seat 513. The fluid is thus blocked from exiting the fluid chamber 505 through the outlet conduit 511.

Figure 6A:
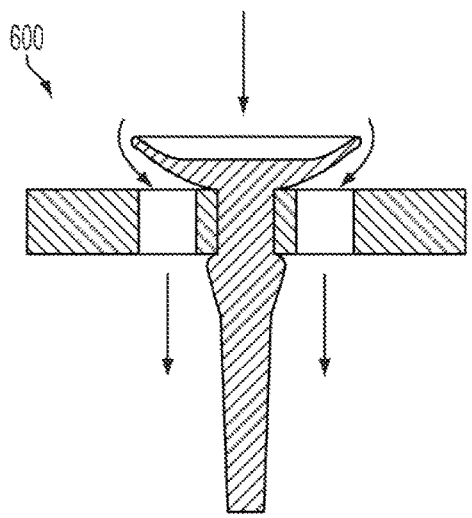
FIGS. 6A-6B illustrate a flow activated valve (FAV) comprising an umbrella valve according to another embodiment.
Figure 6B:
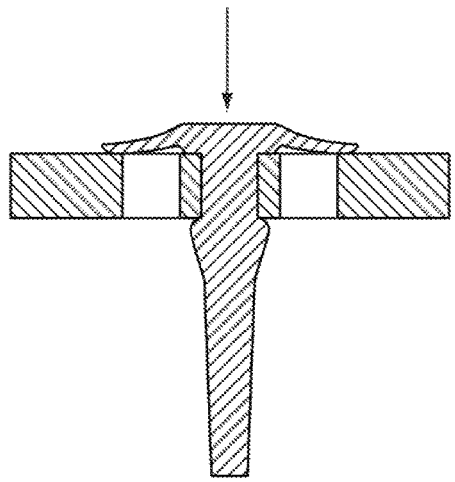

Various alternative configurations of a FAV may be utilized in embodiments. Any bi-stable valve configuration that remains open at a first flow rate/fluid pressure, and closes at or above a threshold flow rate/fluid pressure, higher than the first flow rate/fluid pressure, may be utilized. For example, an umbrella valve 600 may be used, as shown in FIGS. 6A-6B. The umbrella valve 600, which may comprise precision molded silicone rubber, enables fluid flow at normal (metered) flow rates, as shown in FIG. 6A, and seals against a valve seat when the flow rate exceeds a threshold rate, as shown in FIG. 6B.

Figure 7A:
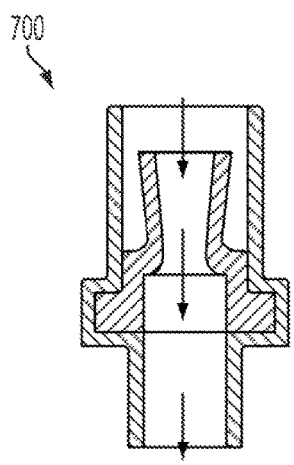
FIGS. 7A-7B illustrate a flow activated valve (FAV) comprising a duck bill valve according to another embodiment.
Figure 7B:
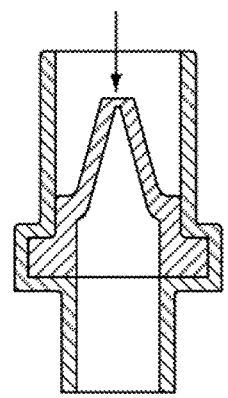

In another embodiment, a FAV may comprise a duck billed valve 700, as shown in FIGS. 7A-7B. The duck billed valve 700, which may comprise precision molded silicone rubber, enables fluid flow at normal (metered) flow rates, as shown in FIG. 7A, and seals against itself (i.e., no valve seat is needed) when the flow rate exceeds a threshold rate, as shown in FIG. 7B.

Figure 8A:
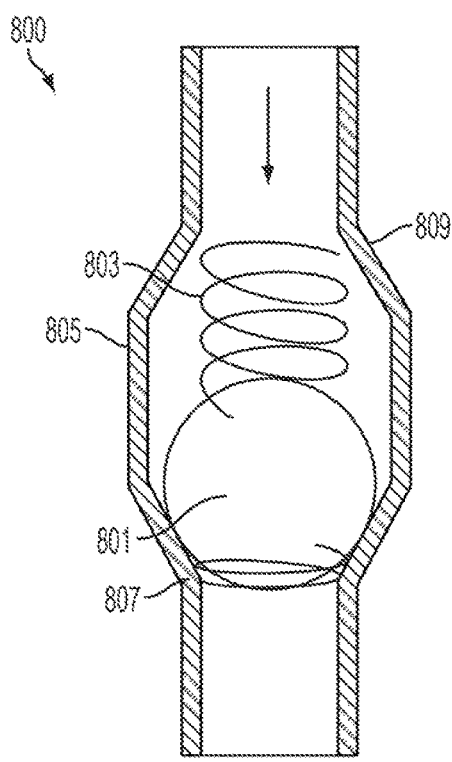
FIGS. 8A-8B illustrate a flow activated valve (FAV) comprising a ball valve according to another embodiment.
Figure 8B:
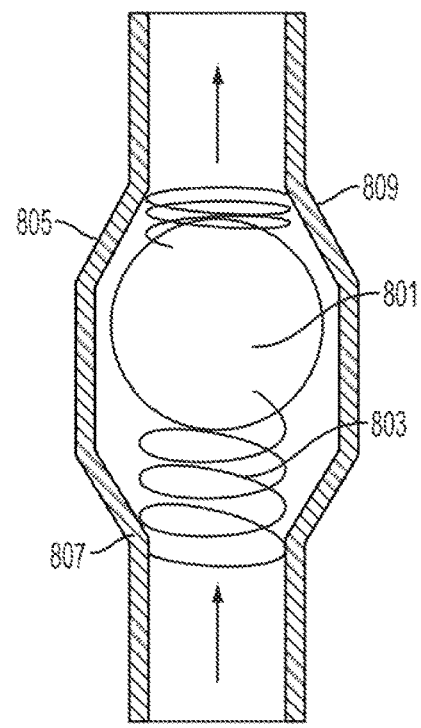

In another embodiment, a FAV may comprise a ball valve 800, as shown in FIGS. 8A-8B. This embodiment may be similar to the FAV 400 utilizing a piston 401 and spring 403, as shown in FIGS. 4A-C. In a typical ball valve design, a ball 801, which may be made of precision molded silicone rubber, is movable within a housing 805 between a first end 807 and a second end 809 of the housing 805. The flow is stopped when the ball 801 is displaced against the first end 807, as shown in FIG. 8A, and is allowed when the ball 801 is displaced against the second end, as shown in FIG. 8B. One or more spring members 803 may bias the ball 801 away from the first end 807. During normal pump operation, the fluid flow is insufficient to overcome the bias force and displace the ball 801 against the first end 807. At or above a threshold flow rate, the ball 801 is displaced against the first end 807 and flow is stopped, as shown in FIG. 8A. The FIG. 8B configuration may enable aspiration of the pump.

Embodiments may further include a release mechanism that causes a closed FAV to return to an open position after the valves 26, 28 are in their closed positions, so that metered flow of the infusate to the patient may be resumed. As described above, a FAV may be bi-stable, meaning that the valve will remain in an open position so long as the fluid flow through the valve does not exceed a threshold flow rate. When the flow rate of the fluid exceeds the threshold flow rate, the valve closes. In general, once the valve is closed, it will stay closed due to the pressure differential across the valve. The FAV may be re-set manually by reducing the pressure from behind the valve (i.e., from the upstream side of the valve). This may cause the FAV to re-set (i.e., return to the open position). Re-setting the FAV may be facilitated by providing a spring force that biases the valve member away from the valve seat, such as via the spring member 403 in FIGS. 4A-4C, or the spring diaphragm 507 of FIGS. 5A-C. The pressure behind the valve may be relieved by, for example, venting the pump reservoir and running the pump empty for a time interval, aspirating through the access port 31, and/or emptying the drug reservoir 10.

In some embodiments, an active or passive FAV release mechanism may be provided that may automatically cause closed FAV to return to an open position. The release mechanism may be configured to re-set the FAV after a particular time period, such as a period equal to or greater than the duration of a typical MRI procedure.

Figure 9:
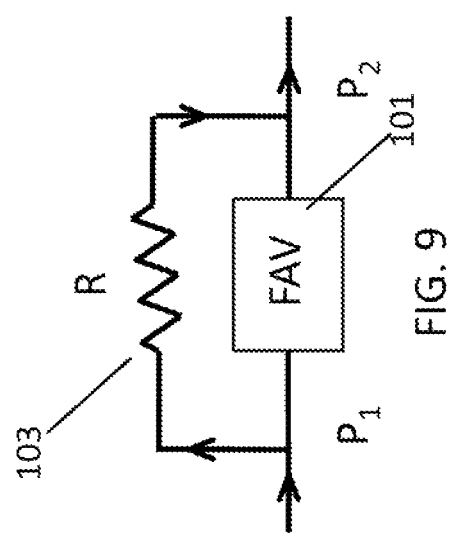
FIG. 9 schematically illustrates a passive FAV release mechanism according to one embodiment.

One embodiment of a passive FAV release mechanism is schematically illustrated in FIG. 9. In this embodiment, a FAV 101 is in closed position. The fluid pressure upstream of the FAV 101 is greater than the fluid pressure downstream of the FAV 101 (i.e., $P_1 > P_2$). The FAV release mechanism in this embodiment comprises a restrictive flow path 103 around and/or through the FAV 101. The FAV 101 may be designed to allow a portion of the fluid on the upstream side of the FAV 101 to leak around or through the FAV 101. The flow rate in the restrictive flow path 103 may be lower than the normal flow rate of the pump, and may be below a clinically acceptable flow rate of the infusate. Allowing a portion of the fluid to flow through the restrictive flow path 103 bleeds off the fluid pressure $P_1$ on the upstream side of the FAV 101. When the upstream fluid pressure $P_1$ falls below a pre-determined pressure, the FAV 101 re-opens. The re-opening of the FAV 101 may be facilitated by a spring force in the FAV 101 that biases the FAV 101 to return to an open position.

Figure 10:
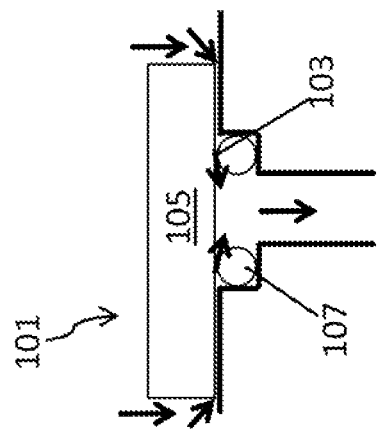
FIG. 10 illustrates an embodiment of a passive FAV release mechanism.

FIG. 10 illustrates one implementation of a restrictive flow path 103 in a closed FAV 101. In this embodiment, the closed FAV 101 includes a valve member 105 contacting a valve seat 107, which may be an o-ring. The interface between the valve member 105 and the valve seat 107 may be designed with a restrictive flow path 103 that enables a small amount of fluid to leak through the interface to the downstream side of the FAV 101. The restrictive flow path 103 may bleed pressure off the back-side of valve member 105, eventually causing valve member 105 to separate from the valve seat 107 and the resumption of normal metered flow of the fluid through the FAV 101. The restrictive flow path 103 may be formed, for example, by providing a highly polished surface of the valve member 105 at the interface with the valve seat 107.

FIGS. 11A-E illustrate further embodiments of a FAV having a restrictive flow path that enables the FAV to bleed pressure from the upstream-side of the valve when it is in the closed position so that the FAV may automatically reset itself to an open position. As shown in FIG. 11A, the FAV 1100 may be similar to the FAV 400 shown in FIGS. 4A-4C, and may include a piston 1101 and spring member 1103 within a housing 1105. The spring member 1103 is configured to bias the piston 1101 away from a valve seat 1107, which may be an O-ring. When the FAV 1100 is in an open position, fluid (e.g., a liquid drug or other infusate) may enter the housing 1105 via an inlet opening 1109, pass around and/or through openings in the piston 1101 and exit the housing 1105 through an outlet opening 1111. When the FAV 1100 is in a closed position, the spring member 1103 is sufficiently compressed so that the piston 1101 contacts and seals against the valve seat 1107, blocking the normal flow of fluid through the FAV. One or more capillary tubes, such as the single capillary tube 1113 shown in FIG. 11A, provides a restrictive flow path that enables a small amount of fluid to flow from the piston housing 1105 to the outlet opening 1111 when the FAV 1100 is in a closed position. This restrictive flow path bleeds pressure off the upstream side of the piston 1101 (i.e., the side of the piston 1101 closest to the inlet opening 1109), eventually causing the piston 1101 to separate from the valve seat 1107, which results in resumption of normal metered flow of the fluid through the FAV 1100. For example, for a valve housing 1105 with a total fluid volume of 1 cc, approximately 0.6 µL of fluid may need to be removed or "bled" from the housing 1105 to relieve sufficient pressure to cause the valve to reset to an open position. A restrictive flow path, such as a capillary tube 1113, with a flow rate of 0.030 mL per day would enable 0.6 µL to be displaced from the housing 1105 in approximately three (3) minutes.

FIG. 11B illustrates a FAV 1102 that is similar to the FAV 1100 illustrated in FIG. 11B. In the embodiment of FIG. 11B, the FAV 1102 includes multiple capillary tubes 1115 that allow small quantities of the fluid to flow from the housing 1105 to the outlet opening 1111 when the FAV 1102 is in a closed position.

FIG. 11C illustrates another embodiment of a FAV 1104 in which a restrictive flow path is provided in the form of a porous material 1117 positioned in a flow path between the housing 1105 and the outlet opening 1111. The porous material 1117 may be configured to allow a small amount of fluid (below a clinically acceptable amount) to flow from the housing 1105 to the outlet opening 1111 when the FAV 1104 is in the closed position. Over time, this flow relieves sufficient pressure from the upstream side of the piston 1101 so that the FAV 1104 eventually returns to an open configuration.

FIG. 11D illustrates another embodiment of a FAV 1106 in which a restrictive flow path is provided in the form of one or more capillary tubes 1119 extending through the piston 1101 to permit a small amount of fluid to flow through the piston 1101 to the outlet opening 1111 when the FAV 1106 is in a closed position. The flow through the capillary tubes 1119 may relieve sufficient pressure from the upstream side of the piston 1101 to cause the FAV 1106 to reset itself to an open position.

FIG. 11E illustrates another embodiment of a FAV 1108 in which a restrictive flow path is provided in the form of a porous material 1121 positioned in the piston 1101 to permit a small amount of fluid (i.e., below a clinically acceptable amount) to flow through the piston 1101 to the outlet opening 1111 when the FAV 1108 is in the closed position. The piston 1101 may further include one or more flow passages 1123 to channel the fluid from the porous material 1121 to the outlet opening 1111 when the FAV 1108 is in the closed position. Over time, this flow relieves sufficient pressure from the upstream side of the piston 1101 so that the FAV 1108 returns to an open configuration.

It will be understood that a FAV may include a passive release mechanism that comprises multiple restrictive flow paths, including various combinations of the restrictive flow paths illustrated in FIGS. 11A-E. In addition, although the embodiments of FIGS. 11A-E depict restrictive flow paths in a FAV that includes a moveable valve member in the form of a spring-biased piston, the various restrictive flow paths shown in FIGS. 11A-E may be utilized in other FAVs, such as the spring diaphragm design of FIGS. 5A-C, the umbrella valve design of FIGS. 6A-B, the duck bill valve design of FIGS. 7A-B, and the ball valve design of FIGS. 8A-B.

Figure 12:
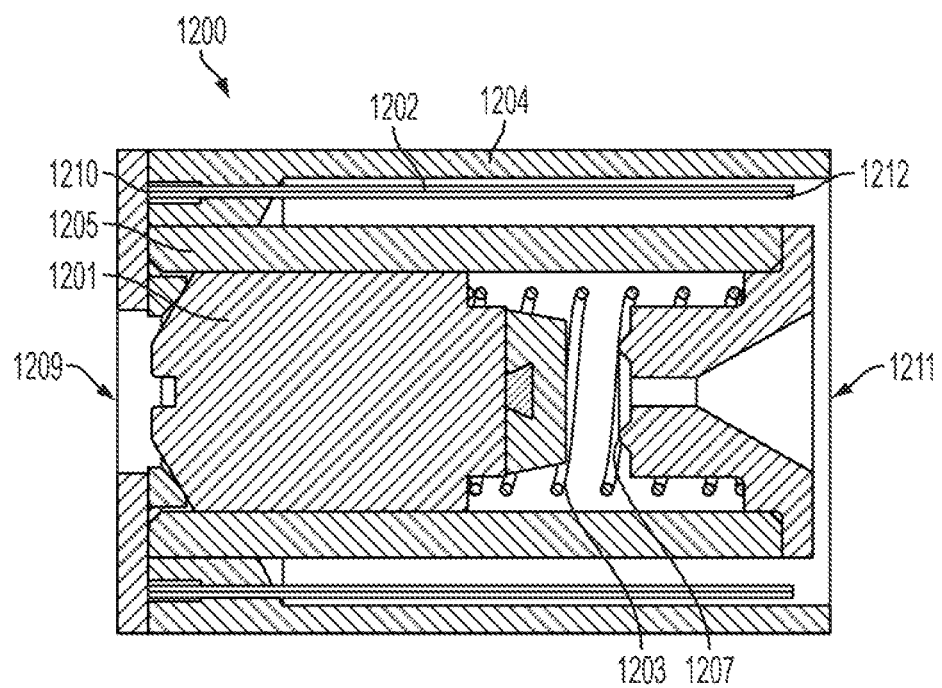
FIG. 12 illustrates an embodiment of a FAV with a release mechanism comprising a plurality of capillary tubes.

FIG. 12 is a cross-section view of another embodiment of a FAV 1200 in which a restrictive flow path is provided in the form of one or more capillary tubes 1202 within an outer sleeve 1204. The FAV 1200 may be similar to the FAV 400 shown in FIGS. 4A-4C, and may include a piston 1201 and spring member 1203 within a housing 1205. The spring member 1203 is configured to bias the piston 1201 away from a valve seat 1207. When the FAV 1200 is in an open position, fluid (e.g., a liquid drug or other infusate) may enter the housing 1205 via an inlet opening 1209, pass around and/or through openings in the piston 1201 and exit the housing 1205 through an outlet opening 1211. When the FAV 1200 is in a closed position, the spring member 1203 is sufficiently compressed so that the piston 1201 contacts and seals against the valve seat 1207, blocking the normal flow of fluid through the FAV. The outer sleeve 1204 may be located around the exterior surface of the housing 1205. The outer sleeve 1204 may be attached to the piston housing 1205, such as via welding or a bonding agent (e.g., an adhesive). One or more capillary tubes 1202 may be provided within the outer sleeve 1204. For example, 1-20 (e.g., 2-8, such as 4) capillary tubes 1202 may be provided in the sleeve 1204. A first end 1210 of each tube 1202 may be in fluid communication with an upstream side of the piston 1201 (i.e., the side of the piston 1201 closest to the inlet opening 1209) and a second end 1212 of each tube 1202 may be in fluid communication with outlet opening 1211. Thus, when the FAV 1200 is in a closed position, as described above, the one or more capillary tubes 1202 provide a restrictive flow path that enables a small amount of fluid to flow through the capillary tubes 1202 from the upstream side of the FAV 1200 (i.e., the side of the FAV 1200 in fluid communication with the inlet opening 1209) to the downstream side of the FAV 1200 (i.e., the side of the FAV 1200 in fluid communication with the outlet opening 1211). This restrictive flow path bleeds pressure off the upstream side of the piston 1201, eventually causing the piston 1201 to separate from the valve seat 1207, which results in resumption of normal metered flow of the fluid through the FAV 1200. In an embodiment, the capillary tube(s) 1202 may permit a fluid flow of 0.01-0.15 mL/day (e.g., 0.05-0.10 mL/day, such as ~0.08 mL/day) through the restrictive flow path, and may provide a FAV reset time of 0.5-3 hours (e.g., ~1 hour) following the closing of the FAV 1200, such as during an MRI procedure.

The capillary tubes 1202 may be formed integrally with the outer sleeve 1204 (e.g., as a channel or opening in the sleeve 1204) or may be formed as a separate structure that may be mounted to or within the sleeve 1204. In some embodiments, one or more capillary tubes 1202 may be formed at the interface between the sleeve 1204 and the exterior surface of the housing 1205 (e.g., as small channels or grooves in the surface of the sleeve 1204 and/or the housing 1205). Further, the capillary tubes 1202 may have any suitable size and shape, and may for example have a cross-section shape that is generally circular, ovoid, polygonal, etc., and which may be uniform or variable over the length of the tube 1202. The capillary tubes 1202 may have a diameter that is uniform or variable along the length of the tube 1202. Further, each of the tubes 1202 within a sleeve 1204 may have a uniform size and shape, or different tubes 1202 within a sleeve 1204 may have different sizes and/or shapes.

In addition, although FIG. 12 illustrates the outer sleeve 1204 as being a separate component from the housing 1205, in some embodiments the housing 1205 of the FAV may serve as the outer sleeve 1204. For example, the capillary tube(s) 1202 may be provided in the housing 1205 rather than in a separate outer sleeve 1204. In addition, although FIG. 12 shows a restrictive flow path in a FAV that includes a moveable valve member in the form of a spring-biased piston, the restrictive flow path shown in an embodiment may be utilized in other FAVs, such as the spring diaphragm design of the embodiments illustrated in FIGS. 5A-C, the umbrella valve design of the embodiments illustrated in FIGS. 6A-B, the duck bill valve design of the embodiments illustrated in FIGS. 7A-B, and the ball valve design of the embodiments illustrated in FIGS. 8A-B.

Figure 13A:
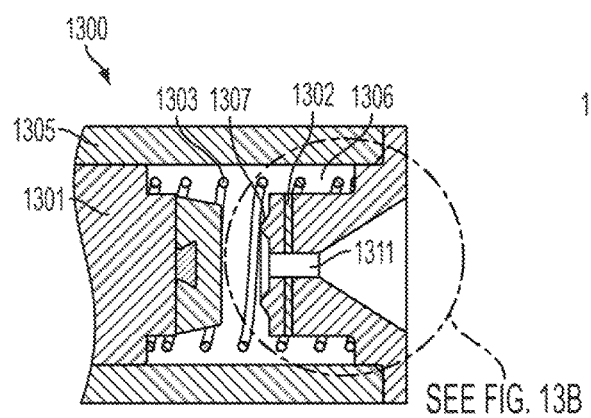
FIGS. 13A-D illustrate an embodiment of a FAV with a release mechanism comprising a disk with fluid channels formed in a surface of the disk.

FIGS. 13A-D illustrate another embodiment of a FAV 1300 with a release mechanism that comprises a disk 1302 having one or more flow channels in a surface of the disk that provide a restrictive flow path between an upstream side and a downstream side of the FAV 1300. FIG. 13A is a partial cross-section view of the FAV 1300 according to this embodiment. This embodiment FAV 1300 may be similar to the embodiment FAV 400 shown in FIGS. 4A-4C, and may include a housing 1305 defining an upstream fluid chamber 1306. The FAV 1300 may further include a moveable piston 1301 and a spring member 1303 within the housing 1305, and the spring member 1303 may be configured to bias the piston 1301 away from a valve seat 1307. When the FAV 1300 is in an open position (i.e., the piston 1301 is not contacting the valve seat 1307), fluid (e.g., a liquid drug or other infusate) may enter the upstream fluid chamber 1306 via an inlet opening (not shown in FIG. 13A), pass through an outlet opening 1310 within the valve seat 1307, and exit the FAV 1300 via an outlet conduit 1311. When the FAV 1300 is in a closed position, the spring member 1303 is sufficiently compressed so that the piston 1301 contacts and seals against the valve seat 1307, blocking the flow of fluid from the upstream fluid chamber 1306 through the outlet opening 1310 to the outlet conduit 1311.

In the embodiment illustrated in FIGS. 13A-D, a passive release mechanism may include a disk 1302 having one or more flow channels in a surface of the disk. The disk 1302 may be positioned in the FAV 1300 such that the one or more flow channels of the disk 1302 are in fluid communication with both the upstream fluid chamber 1306 and the outlet conduit 1311. In the embodiment of FIG. 13A, the disk 1302 may be located behind the valve seat 1307 (i.e., on the side of the valve seat 1307 opposite the piston 1301) and concentrically surround the outlet conduit 1311. Other locations and configurations of the disk 1302 may be utilized. Thus, when the FAV 1300 is in a closed position, as described above, the one or more flow channels in the disk 1302 provide a restrictive flow path that enables a small (e.g., below clinically acceptable) amount of fluid to flow from the upstream fluid chamber 1306 to the outlet conduit 1311 and out of the FAV 1300, thereby bypassing the outlet opening 1300 in the valve seat 1307 which is sealed by the piston 1301. This restrictive flow path bleeds pressure off the upstream side of the piston 1301, eventually causing the piston 1301 to separate from the valve seat 1307, enabling the resumption of normal metered flow of the fluid through the FAV 1300.

Figure 13B:
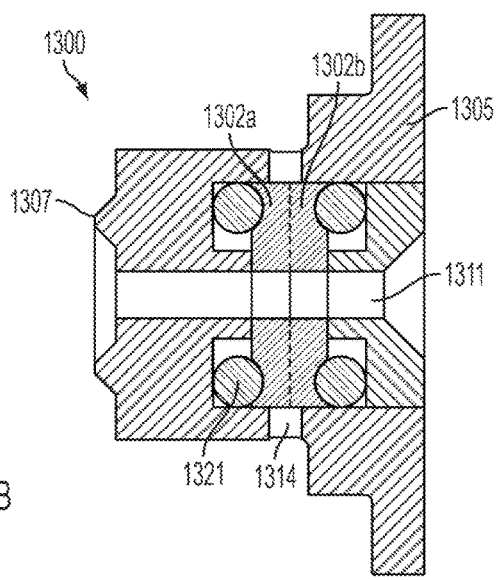

FIG. 13B is an enlarged view of a portion of a FAV 1300 illustrating a passive release mechanism including a disk with flow channels according to an embodiment. In this embodiment, the passive release mechanism includes two disks 1302a, 1302b pressed against one another. One or both disks 1302a, 1302b may include flow channel(s) in the surface of the disk facing the other disk. The disks 1302a, 1302b may be mounted in a portion of the FAV housing 1205 located behind the valve seat 1307 (i.e., on the side of the valve seat 1307 opposite the piston 1301). The disks 1302a, 1302b may concentrically surround the outlet conduit 1311, such that the outlet conduit 1311 extends through an opening 1320 in the disks 1302a, 1302b (see FIG. 13C). Fluid may flow from the upstream fluid chamber 1306 through openings 1314 in the FAV housing 1305 to the outer circumference of disks 1302a, 1302b. The fluid may then enter the one or more flow channels at the interface between the disks 1302a, 1302b, flow through the one or more flow channels, and exit the flow channel(s) at the interior opening 1320 (FIG. 13C) of the disks 1302a, 1302b. The fluid may exit the flow channels into the outlet conduit 1311 and then flow out of the FAV 1300. To prevent unwanted leakage around the disks 1302a, 1302b, the disks 1302a, 1302b may be sealed against the FAV housing 1305, such as with o-rings 1321.

Figure 13C:
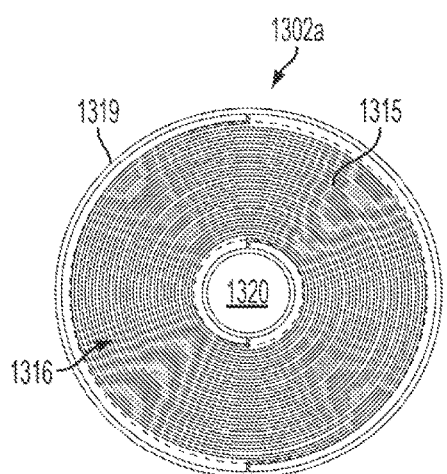

FIG. 13C is an overhead view of a disk 1302a having one or more flow channels 1315 in a first surface 1316 of the disk 1302a. The disk 1302a and channels 1315 may be formed using any suitable material(s) and techniques. For example, the disk 1302a may be a relatively thin structural material (e.g., metal, plastic, glass, ceramic, semiconductor, etc.) and the flow channel(s) 1315 may be formed in a surface 1316 of the disk 1302a in a desired pattern using an appropriate technique, such as via machining, wet or dry etching, laser etching, molding, etc. In an embodiment, the disk 1302a may made from or as a silicon chip and the flow channels 1315 may be formed in a surface of the chip using silicon processing techniques (e.g., photolithography and etching), as are well-known in microelectromechanical system (MEMS) and semiconductor integrated circuit technologies. As an example, the flow channels 1315 may be formed in a continuous helical pattern between the outer circumference 1319 of the disk 1302a and the interior opening 1320 of the disk as illustrated. Multiple flow channels 1315 may be provided in the surface 1316 so that fluid may still flow if one of the channels becomes blocked or occluded. Each flow channel 1215 may have a hydraulic diameter of less than about 1 mm in some embodiments.

Figure 13D:
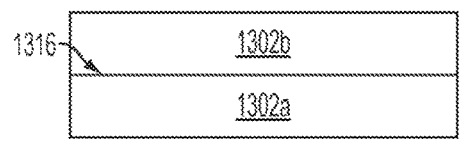

A second disk 1302b may be provided over the patterned surface 1316 of disk 1302a, as shown in the side view of FIG. 13D. In an embodiment, the second disk 1302b may made from the same material (e.g., a silicon disk) and have a similar size and shape as the first disk 1302a, but may not include a patterned surface forming flow channels. In other embodiments, both of the interfacing surfaces of the first and second disks 1302a, 1302b may include flow channels. The second disk 1302b may be secured to the first disk 1302a, such as by laser welding or press-fitting.

Although the disks 1302a, 1302b in this embodiment are shown as generally circular, the term "disk" as used herein refers to any plate-like member having any suitable shape, such as generally circular, oval, polygonal, or irregularly shaped members. Further, while the embodiment shown in FIGS. 13B and 13D includes two disks 1302a, 1302b, various embodiments of a passive release mechanism may have more or less than two disks. For example, a passive release mechanism for a FAV may include a stack or three or more disks in which at least some of the disks in the stack include a surface having flow channel(s) as described above. In addition, embodiments may include a single disk 1302 with flow channel(s) formed in a surface of the disk. The surface of the disk having flow channel(s) may directly interface with an interior surface of the FAV housing 1305. Further, although FIGS. 13A-B shows a restrictive flow path in a FAV that includes a moveable valve member in the form of a spring-biased piston, a disk 1302 with fluid channels as described above may be utilized in other FAVs, such as the spring diaphragm design of the embodiments illustrated in FIGS. 5A-C, the umbrella valve design of the embodiments illustrated in FIGS. 6A-B, the duck bill valve design of the embodiments illustrated in FIGS. 7A-B, and the ball valve design of the embodiments illustrated in FIGS. 8A-B.

In other embodiments, a disk 1302 having one or more flow channels may be incorporated into the piston 1301 and/or valve seat 1307 of the FAV 1300. For example, rather than the disk 1302 being positioned behind (e.g., downstream from) the valve seat 1307, as shown in FIGS. 13A-B, the disk 1302 may be included in the piston 1301. For example, referring to FIGS. 11D and 11E, a disk 1302 having flow channels as described above may provide a restrictive flow path to an interior conduit within the piston (e.g., conduits 1119 and 1123 in FIGS. 11D and 11E, respectively) to enable a small amount of fluid to escape through the closed FAV. In other embodiments, a disk 1302 having fluid channels like those described above may form part of all of the valve seat, such that a piston or other moveable valve member seals against the disk 1302 when the FAV is in the closed position while a small amount of fluid is allowed to pass through the fluid channels in the disk 1302.

In other embodiments, flow channels (e.g., micro-channels) may be formed in the interface between the moveable element of the FAV (e.g., a piston, diaphragm, duck bill valve, umbrella valve, ball valve, as described above) and the portion of the FAV against which the moveable portion seals (e.g., the valve seat) such that a restrictive flow path is provided across this interface when the FAV is in a closed position. A surface finish of the two mating portions of the FAV (e.g., moveable portion and valve seat) may be configured to permit a small quantity of fluid to leak across the valve interface to bleed-off pressure over time and cause the FAV to reset to an open position. In other words, the FAV itself may be intentionally designed as a "leaky valve" to provide a passive reset mechanism for the FAV. Thus, in addition to forming flow channels in one or more of the mating surfaces, a surface texture may be provided on one or more of the surfaces (e.g., by vapor deposition of balls, bumps or other protuberances) that may provide a tortuous path for a small amount of fluid to flow across the valve interface. In other embodiments, one or both of the mating portions of the FAV may comprise a slightly porous material that permits a small leakage flow.

In other embodiments, a FAV may include an active release mechanism. FIG. 14 illustrates one embodiment of a FAV 101 having an active release mechanism. In this embodiment, the active release mechanism comprises an actuator 109, such as a motor, that opens a pressure release chamber 113 on the upstream side of the valve member 105. In this embodiment, the actuator 109 is mechanically coupled to a plunger element 111 that may reciprocate within the release chamber 113 to vary the fluid volume of the chamber 113. When the FAV 101 is in a closed position, the actuator 109 may cause the plunger element 111 to move in the direction of the arrow in FIG. 14. This increases the fluid volume of the chamber 113, and decreases the fluid pressure $P_1$ exerted on the upstream side of valve member 105. When the upstream fluid pressure $P_1$ falls below a pre-determined pressure, the FAV 101 re-opens. The re-opening of the FAV 101 may be facilitated by a spring force in the FAV 101 that biases the FAV 101 to return to an open position.

In addition to a motor, the actuator 109 may be any suitable mechanical actuator, such as a switch or valve. Preferably, the operation of the actuator 109 is not affected by a strong magnetic field, such as experienced during an MRI procedure. In embodiments, an actuator 109 may be used to open a restrictive flow path 103 around or through the FAV, such as described above in connection with FIG. 11, as an alternative to or in addition to the pressure release chamber 113 shown in FIG. 14.

FIG. 15 illustrates another embodiment of embodiment of a FAV 101 having an active release mechanism. In this embodiment, the active release mechanism comprises an actuator 115 that is operable to perturb the interface between the valve member 105 and the valve seat 107 of the FAV 101. For example, the actuator 115 may be a motor-driven piston, a vibrator, an ultrasonic transducer, a piezoelectric actuator, etc., that is operable to perturb the interface between valve member 105 and valve seat 107 and create a leak or other flow path across the FAV. This bleeds off the fluid pressure $P_1$ exerted on the upstream side of valve member 105. When the upstream fluid pressure $P_1$ falls below a pre-determined pressure, the FAV 101 re-opens. The re-opening of the FAV 101 may be facilitated by a spring force in the FAV 101 that biases the FAV 101 to return to an open position.

In various embodiments, the FAV 101 may include a sensor 117 that determines when the FAV 101 is closed. The sensor 117 may be, for example, an electrical or optical sensor that determines when the FAV 101 is in a closed position. In some embodiments, the sensor 117 may be a magnetic sensor that detects a magnetic field indicative of an MRI procedure. The sensor 117 may send a signal to the device electronics module 32 (see FIG. 1) to indicate that the FAV 101 has closed. The electronics module 32 may be programmed to trigger an active reset of the FAV 101 after a pre-determined time period. The pre-determined time period may be equal to or greater than the duration of a typical MRI procedure. In some embodiments, the electronics module 32 may trigger an active re-set of the FAV 101 on a periodic basis. In embodiments, an active reset of the FAV 101 may be triggered by a signal from an external programmer 34 (see FIG. 1).

While several embodiments of a flow activated valve (FAV) and release mechanism are described above in connection with an implantable valve accumulator pump having electrically-actuated solenoid valves, the embodiments may be applicable to a variety of fluid flow systems (e.g., peristaltic pumps, piezoelectric-based pump systems, etc.), and in particular to fluid flow systems that are implantable in a patient or otherwise not easily accessible because the various embodiments may be used to mitigate the effects of an inappropriate pumping or flow condition.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:
1. An implantable infusion apparatus, comprising:
an infusate reservoir;
an outlet configured to direct an infusate to a delivery site;
a fluid path provided between the infusate reservoir and the outlet;

a metering assembly disposed in the fluid path and comprising a first valve, an accumulator, and a second valve, wherein the metering assembly is configured to:
  receive, by the accumulator, the infusate from the infusate reservoir when the first valve is open and the second valve is closed, and
  output, from the accumulator to the fluid path, a metered quantity of the infusate at a first flow rate when the first valve is closed and the second valve is open; and
a flow activated valve disposed upstream or downstream from the metering assembly in the fluid path, wherein the flow activated valve is different from the first valve and the second valve of the metering assembly and is configured to:
  maintain an open position when at most one of the first valve and the second valve of the metering assembly is open thereby allowing the infusate to flow through the flow activated valve at the first flow rate output by the metering assembly, and
  actuate to a closed position such that the infusate is prevented from reaching the outlet, wherein the flow activated valve is actuated to the closed position in response to a rate of flow of the infusate through the flow activated valve exceeding a threshold flow rate greater than the first flow rate output by the metering assembly,
  wherein the threshold flow rate is greater than a maximum expected flow rate during normal operation of the metering assembly, and
  wherein the maximum expected flow rate during the normal operation of the metering assembly is based on a flow rate of the infusate through the flow activated valve when only one of either of the first valve and the second valve of the metering assembly is open.

2. The implantable infusion apparatus of claim 1, wherein the threshold flow rate corresponds to a flow rate indicative of an unrestricted flow of the infusate from the infusate reservoir to the delivery site.

3. The implantable infusion apparatus of claim 1, wherein the first valve and the second valve are solenoid valves.

4. The implantable infusion apparatus of claim 1, further comprising:
  a release mechanism that is operable to re-open the flow activated valve from the closed position.

5. The implantable infusion apparatus of claim 4, wherein the release mechanism is a passive release mechanism.

6. The implantable infusion apparatus of claim 5, wherein the passive release mechanism comprises a restrictive flow path around or through the flow activated valve configured to bleed fluid pressure from an upstream side of the flow activated valve, thereby causing the flow activated valve to re-open.

7. The implantable infusion apparatus of claim 6, wherein the flow activated valve comprises a moveable valve member within a housing having a fluid inlet and a fluid outlet, and the passive release mechanism comprises one or more of a porous material and a capillary tube that provides the restrictive flow path from the fluid outlet of the housing.

8. The implantable infusion apparatus of claim 7, wherein the one or more of the porous material and the capillary tube are located on the moveable valve member.

9. The implantable infusion apparatus of claim 6, wherein the flow activated valve comprises a moveable valve member within a housing having a fluid inlet and a fluid outlet, and the passive release mechanism comprises at least one capillary tube having a first end in fluid communication with the fluid inlet and a second end in fluid communication with the fluid outlet configured so that the at least one capillary tube provides the restrictive flow path around or through the flow activated valve when the flow activated valve is in the closed position.

10. The implantable infusion apparatus of claim 9, wherein the at least one capillary tube is located in at least one of the housing and an outer sleeve that surrounds the housing.

11. The implantable infusion apparatus of claim 6, wherein the flow activated valve comprises a moveable valve member within a housing having a fluid inlet and a fluid outlet, and the passive release mechanism comprises at least one disk having at least one fluid channel in a surface of the at least one disk and positioned such that a first end of the at least one fluid channel is in fluid communication with the fluid inlet and a second end of the at least one fluid channel is in fluid communication with the fluid outlet configured such that the at least one fluid channel provides the restrictive flow path around or through the flow activated valve when the flow activated valve is in the closed position.

12. The implantable, infusion apparatus of claim 11,
  wherein the passive release mechanism comprises at least a first disk and a second disk;
  wherein the first disk and the second disk are two bonded silicon disks,
  wherein the first disk includes at least one fluid channel in a first surface of the first disk; and
  wherein the at least one fluid channel in the first surface of the first disk is formed in the first surface of the first disk using a MEMS-based technology.

13. The implantable infusion apparatus of claim 6,
  wherein the flow activated valve comprises a housing having a moveable valve member having a first interfacing surface and a valve seat having a second interfacing surface, and
  wherein the first interfacing surface contacts the second interfacing surface when the flow activated valve is in the closed position, and the passive release mechanism comprises a surface treatment configured on at least one of the first and second interfacing surfaces to provide the restrictive flow path between the first and second interfacing surfaces.

14. The implantable infusion apparatus of claim 4, wherein the release mechanism is an active release mechanism.

15. The implantable infusion apparatus of claim 14, wherein the active release mechanism comprises a pressure relief chamber configured to be opened when the flow activated valve is closed to reduce fluid pressure from an upstream side of the flow activated valve, thereby causing the flow activated valve to re-open.

16. The implantable infusion apparatus of claim 14, wherein the active release mechanism comprises an actuator configured to perturb an interface between a valve member and a valve seat of the flow activated valve configured to cause the flow activated valve to re-open.

17. The implantable infusion apparatus of claim 16, wherein the actuator comprises at least one of a mechanical actuator, an ultrasonic actuator and a piezoelectric actuator.

18. The implantable infusion apparatus of claim 4, further comprising:
  a sensor configured to detect when the flow activated valve is closed, wherein the release mechanism is configured to be triggered in response to the sensor detecting that the flow activated valve is closed.

19. The implantable infusion apparatus of claim 1,
wherein the flow activated valve comprises a housing having a moveable valve member, and
wherein the flow activated valve is configured such that a fluid pressure in the housing when the rate of flow of the infusate exceeds the threshold flow rate causes the moveable valve member to contact against a valve seat and restrict a flow of the infusate through the flow activated valve.

20. The implantable infusion apparatus of claim 19, wherein the moveable valve member comprises a piston attached to a spring member.

21. The implantable infusion apparatus of claim 19, wherein the moveable valve member comprises a spring diaphragm.

22. The implantable infusion apparatus of claim 19, wherein the moveable valve member is biased away from the valve seat by a spring force.

23. The implantable infusion apparatus of claim 22, wherein the spring force is configured to prevent the moveable valve member from contacting the valve seat at the first flow rate of the infusate.

24. The implantable infusion apparatus of claim 1, wherein the flow activated valve comprises one or more of a ball valve, an umbrella valve, and a duck bill valve.

25. An implantable infusion apparatus, comprising:
means for metering a quantity of an infusate from an infusate reservoir to an outlet of the implantable infusion apparatus at a first infusate flow rate using a first valve and a second valve; and
means for preventing unrestricted flow of the infusate from the infusate reservoir to the outlet,
wherein the means for preventing unrestricted flow of the infusate from the infusate reservoir to the outlet maintains an open position when at most one of the first valve and the second valve is open thereby allowing the infusate to flow through the means for preventing unrestricted flow of the infusate from the infusate reservoir to the outlet at the first infusate flow rate,
wherein the means for preventing unrestricted flow of the infusate from the infusate reservoir to the outlet actuates to a closed position such that the infusate is prevented from reaching the outlet when a flow rate of the infusate through the means for preventing unrestricted flow of the infusate from the infusate reservoir to the outlet exceeds a threshold flow rate greater than the first infusate flow rate,
wherein the means for preventing unrestricted flow of the infusate from the infusate reservoir to the outlet is disposed upstream or downstream from the means for metering the quantity of the infusate from the infusate reservoir to the outlet, and
wherein the threshold flow rate is based on a flow rate of the infusate through the means for preventing unrestricted flow of the infusate from the infusate reservoir to the outlet when both the first valve and the second valve are open.

26. The apparatus of claim 25, wherein the means for preventing unrestricted flow of the infusate from the infusate reservoir to the outlet is configured to be automatically re-opened after the means for preventing unrestricted flow of the infusate from the infusate reservoir to the outlet is closed.

* * * * *